US011992403B2

(12) United States Patent
Berndt et al.

(10) Patent No.: US 11,992,403 B2
(45) Date of Patent: May 28, 2024

(54) DEVICES, SYSTEMS AND METHODS FOR IMPROVING RECAPTURE OF PROSTHETIC HEART VALVE DEVICE WITH STENT FRAME HAVING VALVE SUPPORT WITH INWARDLY STENT CELLS

(71) Applicant: 4C Medical Technologies, Inc., Maple Grove, MN (US)

(72) Inventors: Jonathan Berndt, Crystal, MN (US); Sounthara Khouengboua, Chaska, MN (US); Saravana Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 17/111,736

(22) Filed: Dec. 4, 2020

(65) Prior Publication Data

US 2021/0275297 A1    Sep. 9, 2021

Related U.S. Application Data

(60) Provisional application No. 62/989,209, filed on Mar. 13, 2020, provisional application No. 62/988,421, (Continued)

(51) Int. Cl.
*A61F 2/24* (2006.01)
*A61F 2/95* (2013.01)

(52) U.S. Cl.
CPC .......... *A61F 2/2418* (2013.01); *A61F 2/2427* (2013.01); *A61F 2/95* (2013.01); *A61F 2002/9511* (2013.01)

(58) Field of Classification Search
CPC ........ A61F 2/2418; A61F 2/2427; A61F 2/95; A61F 2002/9511; A61F 2/2439; A61F 2002/9528; A61F 2230/0071
See application file for complete search history.

(56) References Cited

U.S. PATENT DOCUMENTS

| 4,424,833 A | 1/1984 | Spector |
| 4,503,569 A | 3/1985 | Dotter |

(Continued)

FOREIGN PATENT DOCUMENTS

| AU | 2014203064 B2 | 6/2015 |
| AU | 2015230879 A1 | 10/2015 |

(Continued)

OTHER PUBLICATIONS

International Search Report and Written Opinion issued in PCT application No. PCT/US2020/63591, dated Mar. 2, 2021.

(Continued)

*Primary Examiner* — Bruce E Snow
(74) *Attorney, Agent, or Firm* — Weiss & Arons LLP

(57) ABSTRACT

A collapsible and expandable prosthetic mitral valve stent is provided with improved recapture into a distal lumen of a delivery sheath. Various embodiments comprise a valve support within the interior of a stent frame and defining a flow channel therethrough, wherein the top or upstream of the valve support comprises a row, or a plurality, of stent cells that are bent radially inward at least partially over the flow channel. Some embodiments may comprise a recapture assist mechanism, such as an open paddle, attached to one or more of the inwardly bent stent cells and adapted to receive and/or engage a wire to aid in positioning, expansion, recapture and/or implanting the device in a patient's heart chamber.

17 Claims, 11 Drawing Sheets

Related U.S. Application Data filed on Mar. 12, 2020, provisional application No. 62/987,413, filed on Mar. 10, 2020, provisional application No. 62/986,151, filed on Mar. 6, 2020.

(56) References Cited

U.S. PATENT DOCUMENTS

| | | |
|---|---|---|
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,231,602 B1 | 5/2001 | Carpentier |
| 6,287,334 B1 | 9/2001 | Moll |
| 6,319,280 B1 | 11/2001 | Schoon |
| 6,319,281 B1 | 11/2001 | Patel |
| 6,332,893 B1 | 12/2001 | Mortier |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,569,196 B1 | 5/2003 | Vesely |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | DiMatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,252,682 B2 | 8/2007 | Seguin |
| 7,276,077 B2 | 10/2007 | Zadno-Azizi |
| 7,276,078 B2 | 10/2007 | Spenser |
| 7,291,168 B2 | 11/2007 | Macoviak |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,611,534 B2 | 11/2009 | Kapadia |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,967,853 B2 | 6/2011 | Eidenschink |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| 8,029,556 B2 | 10/2011 | Rowe |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,252,051 B2 | 8/2012 | Chau |
| 8,287,538 B2 | 10/2012 | Brenzel et al. |
| 8,308,798 B2 | 11/2012 | Pintor |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,644 B2 | 4/2013 | Quadri |
| 8,414,645 B2 | 4/2013 | Dwork |
| 8,439,970 B2 | 5/2013 | Jimenez |
| 8,454,686 B2 | 6/2013 | Alkhatib |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,354 B2 | 8/2014 | Benichou |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |

(56) References Cited

U.S. PATENT DOCUMENTS

| | | |
|---|---|---|
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | McGuckin, Jr. |
| 9,144,493 B2 | 9/2015 | Carr |
| 9,144,494 B2 | 9/2015 | Murray |
| 9,155,619 B2 | 10/2015 | Liu |
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr. |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola et al. |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | McLean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,758,342 B2 | 9/2020 | Chau |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |
| 11,154,396 B2 | 10/2021 | Dibie |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |

(56) References Cited

U.S. PATENT DOCUMENTS

| | | |
|---|---|---|
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |
| 11,458,013 B2 | 10/2022 | Righini |
| 2001/0005787 A1 | 6/2001 | Oz |
| 2002/0072710 A1 | 6/2002 | Stewart |
| 2002/0161377 A1 | 10/2002 | Rabkin |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1 | 6/2005 | Griffin |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0016288 A1 | 1/2007 | Gurskis |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197193 A1 | 8/2012 | Krolik et al. |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1* | 6/2013 | Yohanan ............... A61F 2/2409 623/2.14 |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1* | 12/2013 | Alkhatib ............... A61F 2/2418 623/2.37 |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |

(56) References Cited

U.S. PATENT DOCUMENTS

| | | |
|---|---|---|
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramanian |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | McNamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0328000 A1 | 11/2015 | Ratz et al. |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |

(56) References Cited

U.S. PATENT DOCUMENTS

| | | |
|---|---|---|
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | McCann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | McKinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0242905 A1* | 8/2016 | Chambers ............... A61F 2/243 |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand et al. |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0055629 A1 | 3/2018 | Oba et al. |
| 2018/0092744 A1 | 4/2018 | Von Oepen |
| 2018/0116843 A1 | 5/2018 | Schreck |
| 2018/0116848 A1 | 5/2018 | McHugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | De Haan et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0224028 A1 | 7/2019 | Finn |
| 2019/0247189 A1 | 8/2019 | Dale |
| 2019/0247190 A1 | 8/2019 | Nathe |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1* | 12/2019 | Chambers ............. A61F 2/2454 |
| 2020/0000592 A1 | 1/2020 | Lee |
| 2020/0030088 A1 | 1/2020 | Vidlund |
| 2020/0030507 A1 | 1/2020 | Higgins |
| 2020/0069423 A1 | 3/2020 | Peterson |
| 2020/0069449 A1 | 3/2020 | Diedering |
| 2020/0100897 A1 | 4/2020 | McLean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |

(56) References Cited

U.S. PATENT DOCUMENTS

| | | |
|---|---|---|
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson |
| 2021/0236276 A1 | 8/2021 | Diedering |
| 2021/0275301 A1 | 9/2021 | Kumar |
| 2021/0290383 A1 | 9/2021 | Chambers |
| 2022/0031451 A1 | 2/2022 | Spence |
| 2022/0338979 A1 | 10/2022 | Benichou |
| 2023/0218397 A1 | 7/2023 | Chambers et al. |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 102036622 | 4/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 108348270 | 7/2018 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |
| WO | WO2019006387 | 1/2019 |

OTHER PUBLICATIONS

International Search Report and Written Opinion in Application No. PCT/US2020/063591, dated Mar. 2, 2021.

Reed Miller, Start-Up Spotlight: 4C Addresses Mitral Regurgitation with Unique 'Dome' Device, https://medtech.citeline.com/MT105076/StartUp-Spotlight-4C-Addresses-Mitral-Regurgitation-With-Unique-Dome-Device Published by Citeline on Jun. 29, 2017.

A Novel Transcatheter Mitral Valve Replacement System, Dr. Phillippe Genereux, MD, Jun. 14, 2017.

The Alta Valve™. Attributes, Challenges, and Future Programs, Dr. Philippe Genereux, MD, Jun. 22, 2018.

Goel et al., "Transcatheter Mitral Valve Therapy with Novel Supra-Annular Alta Valve," https://doi.org/10.1016/j.jaccas.2019.10.034, Published by Elsevier on behalf of The American College of Cardiology Foundation, Dec. 18, 2019.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

The Alta Valve™M. Attributes, Challenges, and Future Programs, Dr. Philippe Genereux, MD, Jun. 22, 2018.

4C Medical's Alta Valve: The First-in-Human Experience, Josep Rodes-Cabau, MD, Sep. 21, 2018.

Ferreira-Neto et al., "Transcatheter Mitral Valve Replacement With a New Supra-Annular Valve-First-in-Human Experience with the AltaValve System," https://doi.org/10.1016/j.jcin.2018.10.056, By The American College of Cardiology Foundation Published by Elsevier, Jan. 28, 2019.

Extended European Search Report in Application No. 20923500.1, Feb. 21, 2024.

* cited by examiner

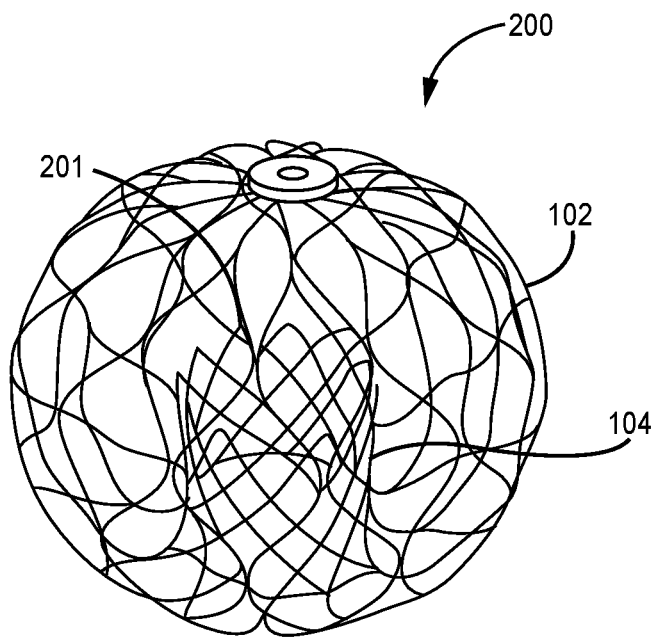
FIG. 8
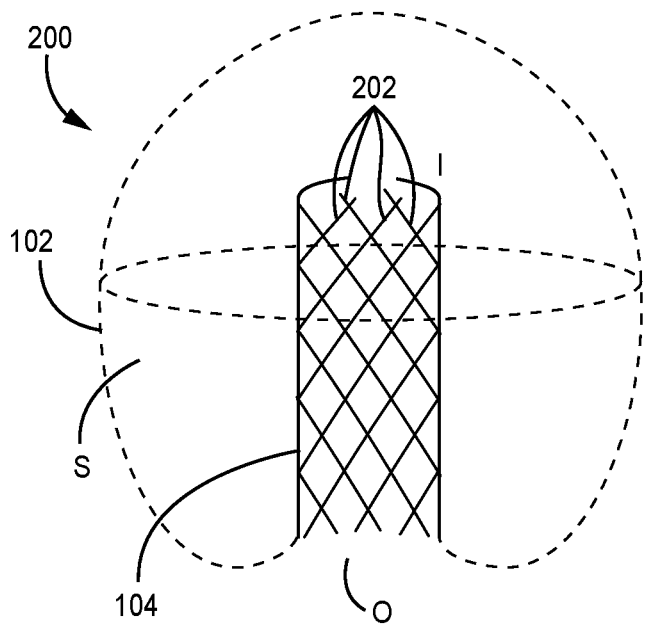 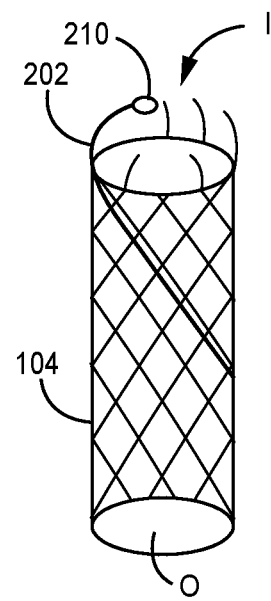
FIG. 9A  FIG. 9B

DEVICES, SYSTEMS AND METHODS FOR IMPROVING RECAPTURE OF PROSTHETIC HEART VALVE DEVICE WITH STENT FRAME HAVING VALVE SUPPORT WITH INWARDLY STENT CELLS

CROSS-REFERENCE TO RELATED APPLICATIONS

This application claims the benefit of U.S. Provisional Application No. 62/986,151, filed Mar. 6, 2020 and entitled DEVICES, SYSTEMS AND METHODS FOR IMPROVING RECAPTURE OF PROSTHETIC HEART VALVE DEVICE WITH STENT FRAME HAVING VALVE SUPPORT WITH INWARDLY STENT CELLS, U.S. Provisional Application No. 62/987,413, filed Mar. 10, 2020 and entitled DEVICES, SYSTEMS AND METHODS FOR IMPROVING RECAPTURE OF PROSTHETIC HEART VALVE DEVICE WITH STENT FRAME HAVING VALVE SUPPORT WITH ELONGATED SECTION, U.S. Provisional Application No. 62/988,421, filed Mar. 12, 2020 and entitled DEVICES, SYSTEMS AND METHODS FOR IMPROVING RECAPTURE OF PROSTHETIC HEART VALVE DEVICE WITH STENT FRAME HAVING VALVE SUPPORT WITH INWARDLY BENT STRUTS and U.S. Provisional Application No. 62/989,209, filed Mar. 13, 2020 and entitled DEVICES, SYSTEMS AND METHODS FOR IMPROVING RECAPTURE OF PROSTHETIC HEART VALVE DEVICE WITH STENT FRAME HAVING VALVE SUPPORT WITH ATTACHMENT TO THE OUTER STENT, the entirety of which are hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to devices, systems and features for improving collapsing and/or recapturing efficiency for a collapsible and expandable prosthetic heart valve device.

Description of the Related Art

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation. As is shown, normal blood flow proceeds through the mitral valve from the left atrium to the left ventricle impinging on the posterior lateral side of the left ventricle (as opposed to the septal side). This natural flow takes advantage of the left ventricular anatomy so that the flow is further directed downward within the left ventricle and then upward toward the aortic valve and the left ventricular outflow tract (LVOT) and the associated aortic root, and ultimately into the ascending aorta as shown. Generally, this flow in normal patients is laminar and, therefore, an efficient mechanism.

FIG. 2 illustrates the relationship between the left atrium, annulus, chordae tendineae and the left ventricle relative to the mitral valve leaflets. As is shown, the upper surface of the annulus forms at least a portion of the floor or lower surface of the left atrial chamber, so that for purposes of description herein, the upper surface of the annulus is defined as marking the lower boundary of the left atrial chamber.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure. FIG. 3 illustrates regurgitant blood flow with an exemplary dysfunctional mitral valve.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, all known prosthetic heart valves are intended for full replacement of the native heart valve. Therefore, these replacement heart valves, and/or anchoring or tethering structures, physically extend out of the left atrial chamber, in the case of mitral valves, and engage the inner annulus and/or valve leaflets, in many cases pinning the native leaflets against the walls of the inner annulus, thereby permanently eliminating all remaining functionality of the native valve and making the patient completely reliant on the replacement valve. In other cases, the anchoring structures extend into the left ventricle and may anchor into the left ventricle wall tissue and/or the sub-annular surface at the top of the left ventricle. Others may comprise a presence in, or engagement with, a pulmonary artery.

Obviously, there will be cases when native valve has lost virtually complete functionality before the interventional implantation procedure. In this case the preferred solution will comprise an implant that does not extent outside of, e.g., the left atrium, and that functions to completely replace the native valve function. However, in many other cases, the native valve remains functional to an extent and may, or may not, continue to lose functionality after the implantation procedure. A preferred solution in this case comprises delivery and implantation of a valve device that will function both as a supplemental or augmentation valve without damaging the native leaflets in order to retain native valve leaflet functionality as long as present, while also being fully capable of replacing the native function of a valve that slowly loses most or all of its functionality post-implantation of the prosthetic valve.

Finally, known prosthetic cardiac valves consist of two or three leaflets that are arranged to act as a one-way valve, permitting fluid flow therethrough in the antegrade direction while preventing retrograde flow. The native mitral valve is located retrosternally at the fourth costal cartilage, consisting of an anterior and posterior leaflet, chordae tendinae, papillary muscles, ventricular wall and annulus connected to the atria. Each native leaflet is supported by chordae tendinae that are attached to papillary muscles which become taut with each ventricular contraction preserving valvular competence. Both the anterior and posterior leaflets of the native valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the native mitral leaflets. In the case of a single mitral valve leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

Known implantable prosthetic valves may be improved upon by employing structures that may aid in the recapture of the devices into the lumen of a delivery sheath.

Certain inventive embodiments described herein are readily applicable to single or two chamber solutions, unless otherwise indicated. Moreover, certain embodiments discussed herein may be applied to preservation and/or replacement of native valve functionality generally, with improved native leaflet coaptation and/or prolapsing, and are not, therefore, limited to the mitral valve and may be extended to include devices and methods for treating the tricuspid valve, the aortic valve and/or pulmonary valves.

Various embodiments of the several inventions disclosed herein address these, inter alia, issues.

BRIEF DESCRIPTION OF THE SEVERAL VIEWS OF THE DRAWINGS

FIG. 8 illustrates a perspective view of one embodiment of a prosthetic heart valve device of the present invention.

FIG. 9A illustrates a cutaway view of one embodiment of a prosthetic heart valve device of the present invention.

FIG. 9B illustrates one embodiment of a prosthetic heart valve device of the present invention.

DETAILED DESCRIPTION OF THE INVENTION

Generally, various embodiments of the present invention are directed to devices and methods for recapture into a distal lumen of a delivery sheath during the expansion and implantation processes. Various embodiments comprise a valve support within the interior of a stent frame and defining a flow channel therethrough, wherein the top or upstream of the valve support comprises a row of stent cells that are bent radially inward at least partially over the flow channel. Some embodiments may comprise a recapture assist mechanism, such as an open paddle, attached to one or more of the inwardly bent stent cells and adapted to receive and/or engage a wire to aid in positioning, expansion, recapture and/or implanting the device in a patient's heart chamber.

Figure 1:
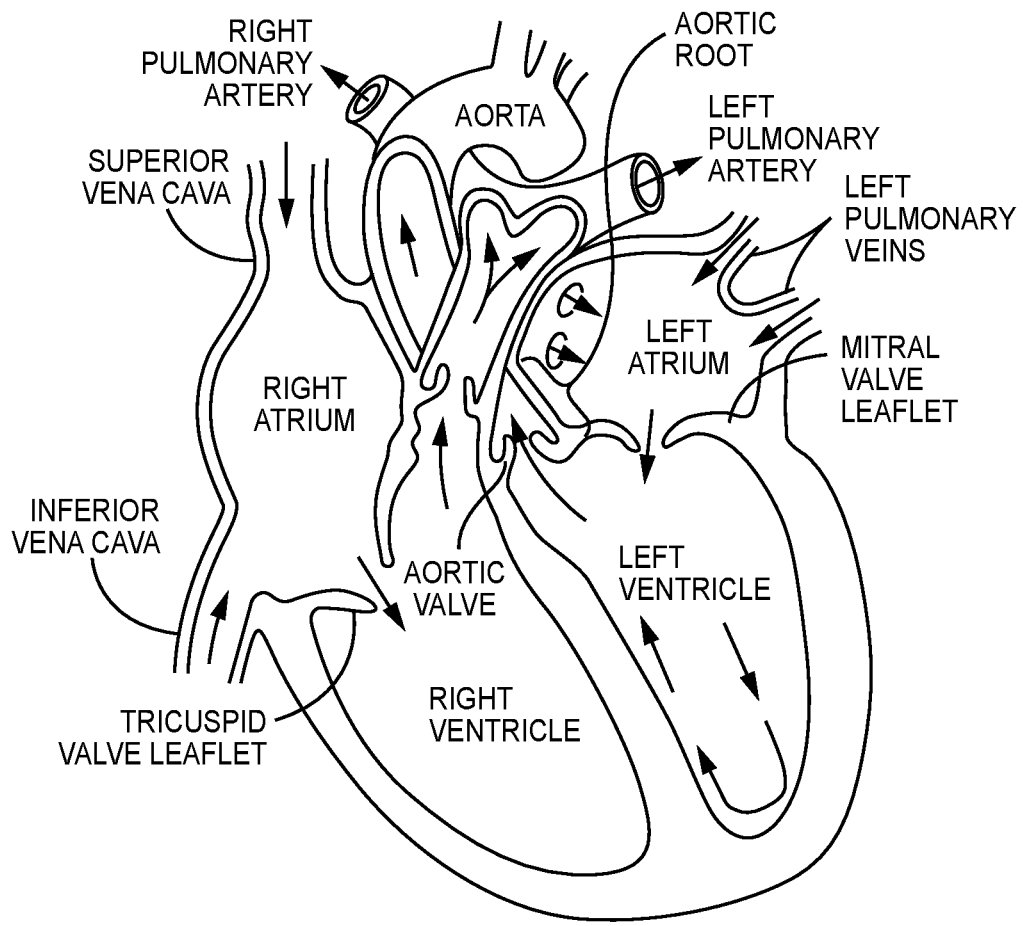
FIG. 1 illustrates certain features of the heart in cross-section.
Figure 2:
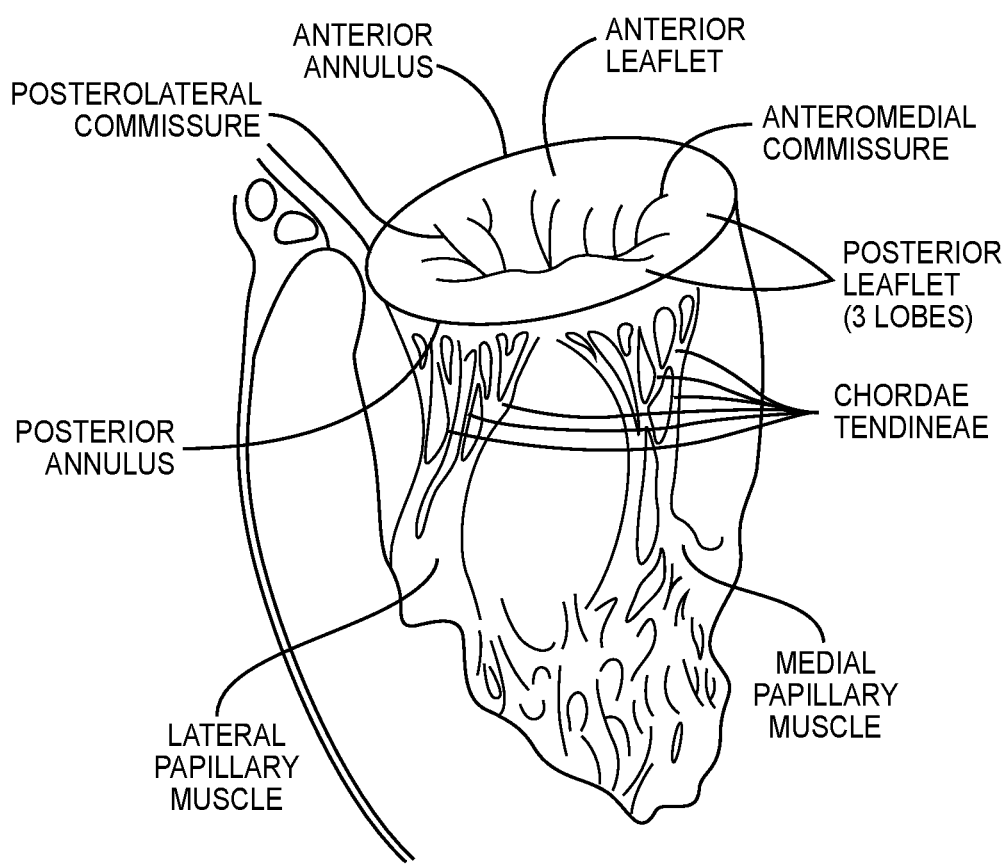
FIG. 2 illustrates a cross-sectional perspective view of the left side of the heart.
Figure 3:
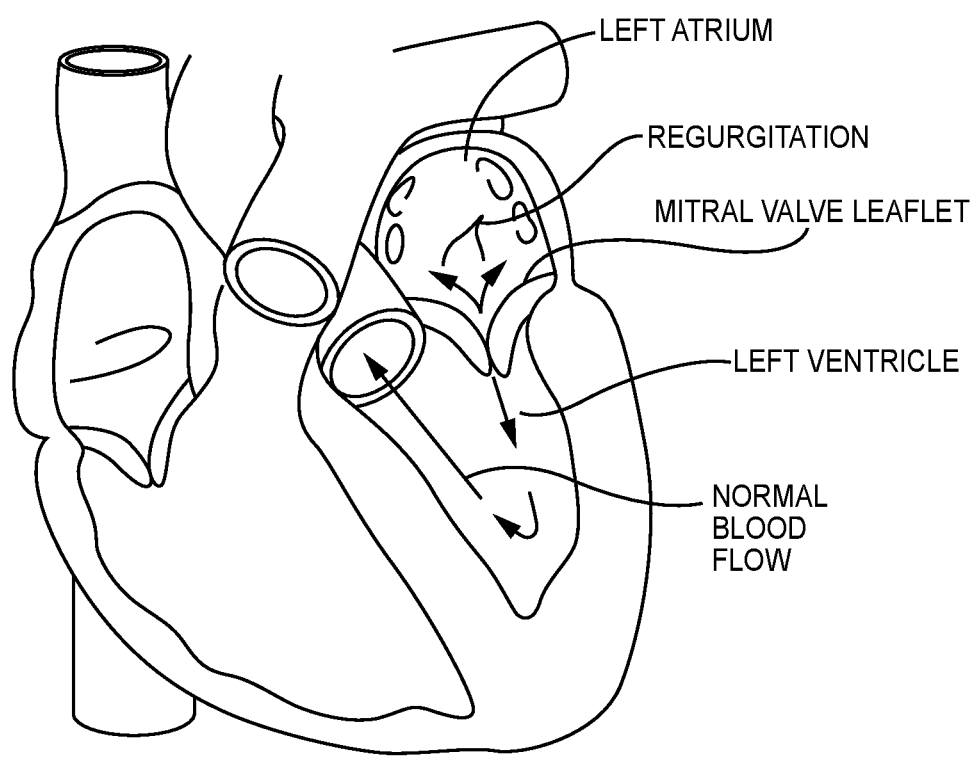
FIG. 3 illustrates a cross-sectional view of the heart showing retrograde blood flow resulting from mitral valve regurgitation compared with normal blood flow.
Figure 4:
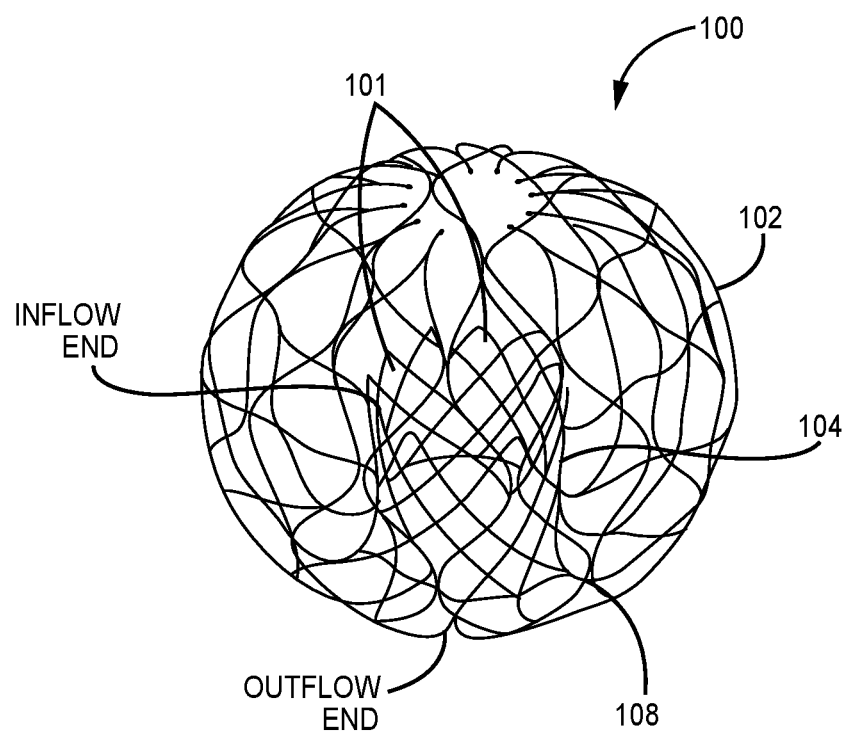
FIG. 4 illustrates a perspective view of a prosthetic heart valve device.
Figure 5:
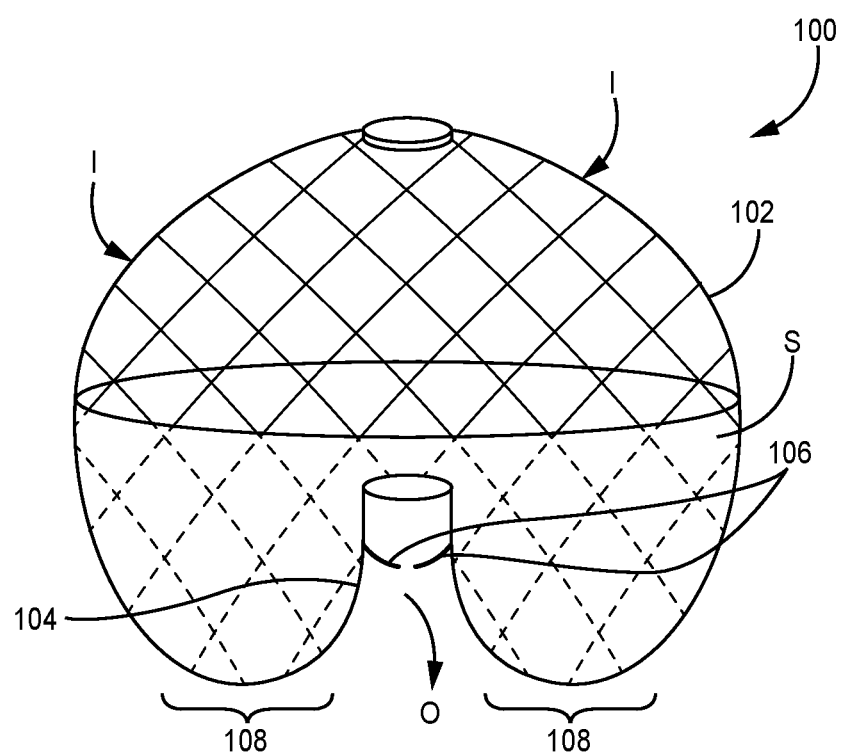
FIG. 5 illustrates side and partial cutaway view of a prosthetic heart valve device.

Turning now to FIGS. 4 and 5, an exemplary embodiment is illustrated of an expandable and collapsible prosthetic heart valve stent 100 may comprise an outer section 102 that may generally look like a ball when undeformed and fully expanded and an inner valve support section 104, adapted to support and retain prosthetic valve leaflets 106 within the inner valve support section 104, most preferably at a point that located above the native annulus, and spaced away or above the native leaflets, as shown, though other attachment points for the prosthetic leaflets 106 are within the scope of the present invention. Inner valve support 104 may be cylindrical, but in a preferred embodiment may also be at least partially conical with a larger diameter at an outflow end O than the diameter across at least portions of an inflow end I, wherein the inflow end I is disposed radially inside the outer frame section and wherein the outflow end may define a lower end or edge of the valve support 104. Thus, in a purely conical arrangement, the valve support section 104 may comprise a smoothly decreasing diameter thereacross and this smooth diameter decrease may extend from the outflow end O to the inflow end I. In other embodiments, the inflow end I may comprise one or more lobes extending radially outwardly and that interrupt the smooth conical profile. A preferred embodiment in this regard provides one lobe for each prosthetic leaflet 106 attached within the inner valve support 104 to allow for fuller freedom of movement and improved coaptation.

A preferred construction comprises the prosthetic leaflets 106 disposed or spaced above the native leaflets when the prosthetic valve stent device 100 is implanted, wherein the prosthetic leaflets 106 are attached and spaced sufficiently away from (above) the native leaflets so as to not physically interfere or interact with the native leaflets and the resulting blood flow.

The layer of stent cells that transition from the outer section to the inner section of the stent are termed as transition cells forming a transition section 108 generally as illustrated in FIGS. 4 and 5.

The outer and inner sections of the stent may be constructed from one continuous structure or may combine two or more structures to achieve intended design goals. As known in the art, stent structures may be formed using complementary shaped mandrels, including the outer section 102 of the stent, the transition section 108, and the inner valve support 104—including lobes L discussed above in certain embodiments—as a single unitary structure.

In certain embodiments, the outer support structure may be positioned generally so that it engages with tissue and works to prevent paravalvular leakage (PVL). For example, the outer support structure of the prolapse prevention structure may engage, or be integrated with, the transition section described above to provide a barrier against PVL.

Further in this regard, a preferred embodiment of the device shown in the Figures comprises a skirt S, comprising fabric or tissue, disposed along a portion of the outer surface of the outer frame element 102 and that extends along the outer surface of the transition section 108 and along the inner surface, or inwardly facing surface, of the inner valve support 104 so that the skirt S is facing the flow channel defined therein from the inflow end I to the outflow end O.

The embodiment of FIG. 4, and certain embodiments of FIG. 5, comprises a top-most (or upstream) set of stent cells 101 in the valve support 104 that are generally directed in the upstream direction. Stated differently, the top-most set of stent cells of valve support 104 define the top of the valve support 104.

Figure 6:
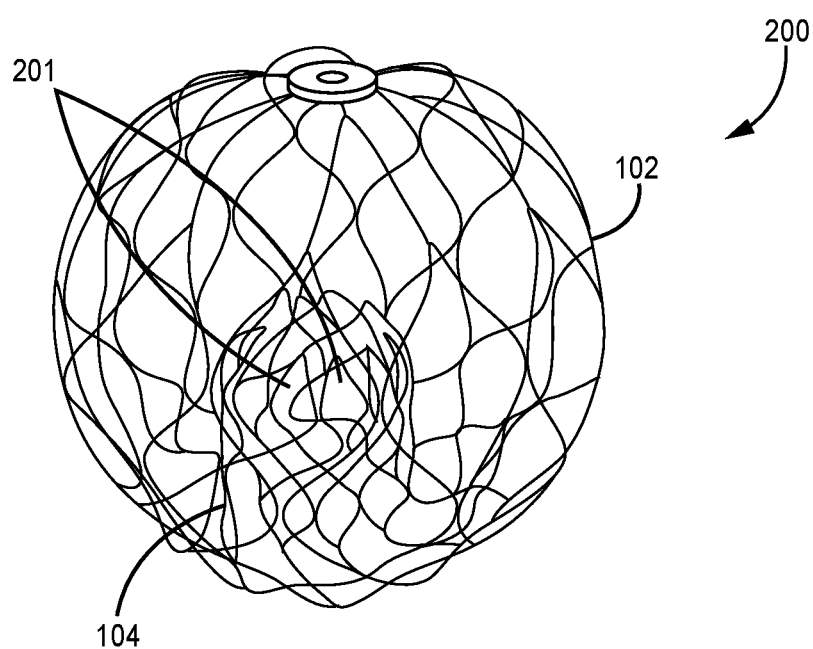
FIG. 6 illustrates a perspective view of one embodiment of a prosthetic heart valve device of the present invention.

Turning now to FIG. 6, a modified and improved prosthetic heart valve device 200 is provided with the same elements as described above in connection with FIGS. 4 and 5, except that the top-most (upstream) stent cells 101 of the valve support 104 now bent radially inward at 201 and over the inflow end of the valve support 104 and the defined blood flow channel therethrough.

Figure 7:
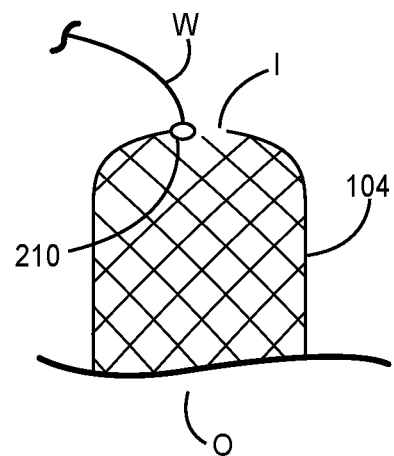
FIG. 7 illustrates a cutaway view of one embodiment of a prosthetic heart valve device of the present invention.

FIG. 7 illustrates a recapture assist mechanism, e.g., a paddle or slot at 210 disposed on, or defined by, one or more of inwardly bent stent cells 201. A single recapture assist mechanism 210 is shown, but more than one may be provided as well. The recapture assist mechanism(s) 210 may be used to receive a wire, e.g., a push and/or pull wire W as is well known in the art, that may be looped or otherwise engage the recapture assist mechanism(s) 210 for aid in directional positioning during delivery and expansion, during recapture/resheathing, or in directional positioning and expanded implantation following recapture/resheathing.

Alternatively, as shown in FIGS. 8 and 9A-9B, a modified and improved heart valve device 200 is provided with the same elements as described above in connection with FIGS. 4-6, except that that the top-most (upstream) stent cells 101 of the valve support 104 now comprise single struts 202 that are bent radially inward and over the inflow end of the valve support 104 and the defined blood flow channel therethrough.

FIG. 9B further illustrates recapture assist mechanism, e.g., a paddle or slot 210 as described above, disposed on the end (upstream and free) portion of one or more of single struts 202. A single recapture assist mechanism 210 is shown, but more than one may be provided. The recapture assist mechanism(s) 210 may be used to receive a wire that may be looped around or through or otherwise engage recapture assist mechanism(s) 210 for aid in directional positioning during delivery and expansion, during recapture and/or resheathing, or in directional positioning and expanded implantation following recapture and/or resheathing.

Figure 10:
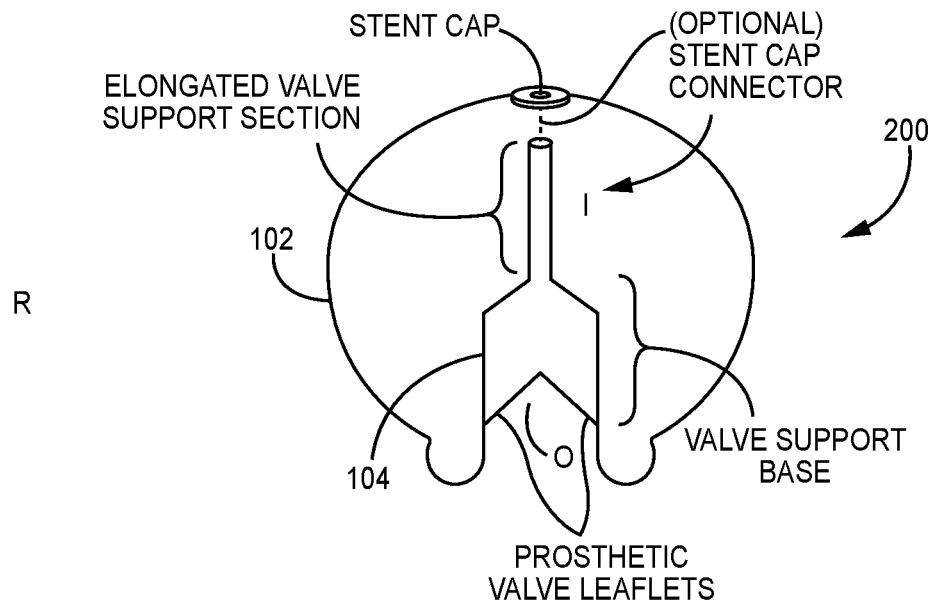
FIG. 10 illustrates a cutaway view of one embodiment of a prosthetic heart valve device of the present invention.

Turning now to FIG. 10, a modified and improved prosthetic heart valve device 200 is provided with the same elements as described above in connection with FIGS. 4 and 5, except that the valve support 104 now comprises an elongated valve support section disposed upstream of the valve support base.

The elongated valve support section may be connected to the stent cap by a stent cap connector such as a wire or strut or other equivalent connecting mechanism or structure. The stent cap comprises a hole or slot for engaging a delivery wire such as a push and/or pull wire to aid in delivery and recapture and/or repositioning of the collapsible and expandable stent device 200.

Figure 11:
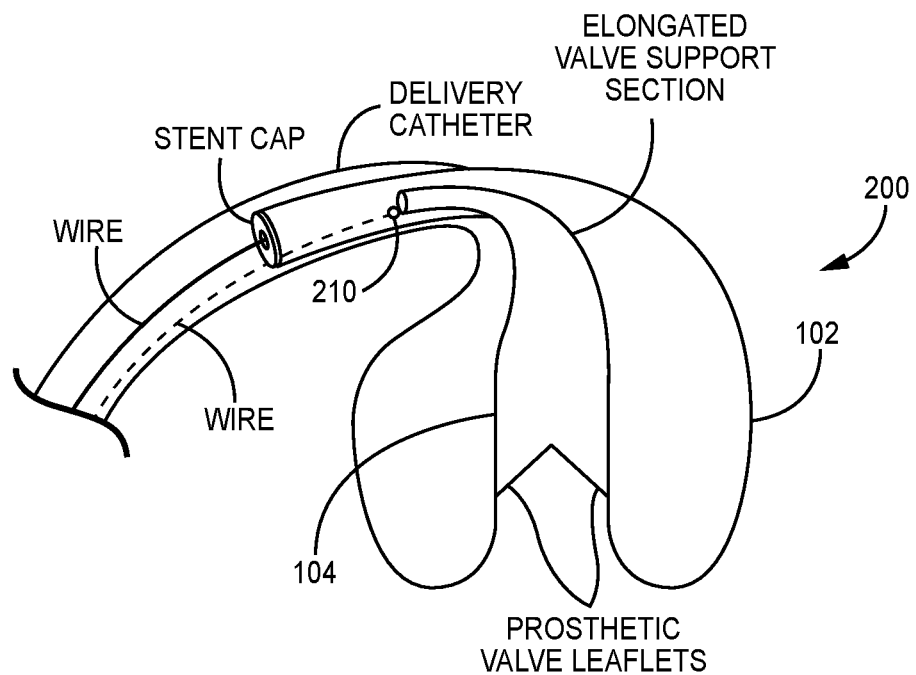
FIG. 11 illustrates a cutaway view of one embodiment of a prosthetic heart valve device of the present invention.

In addition to an optional connection between the elongated valve support and the stent cap as shown in FIG. 10, FIG. 11 illustrates optional recapture assist and/or delivery assist mechanism at 210, as described herein, which may be a loop or an open paddle and that is adapted for receiving and/or engaging a wire that extends through lumen of delivery catheter to aid in manipulating the elongated valve support section. Mechanism 210 may be attached or formed at any point along the length (or at the top-most or upstream end) of elongated valve support section.

Skirt S (not shown in FIG. 10 or 11) may cover the inner portion of valve support 104 (thereby forming at least part of the blood flow channel defined therein). In some embodiments, the elongated section of the valve support 104 may comprise skirt S on the inner section or may not comprise skirt S.

In some embodiments, the elongated valve support section is in fluid communication with the valve support base and may admit blood into valve support. In this case, the defined blood flow channel may comprise at least part of the elongated valve support section in combination with the valve support base.

FIG. 11 illustrates delivery of the partially expanded prosthetic heart valve device 200 out of a delivery catheter lumen and into a subject heart chamber, e.g., the left atrium. As shown, a transseptal delivery technique may comprise the outer section 102 of the device 200 being expanded and fully deployed while at least a portion of the elongated valve support section, and the upper portion of the outer section 102 including the stent cap, may remain within the lumen of the delivery catheter. The embodiment shown does not provide a connection between the stent cap and the elongated valve support section, but does provide a wired connection with the stent cap and the proximally located operator, as well as recapture and/or delivery assist mechanism 210 connected or engaged wire also extending through lumen of the delivery catheter to a proximally located operator.

Thus, if recapture or resheathing is required, the entire device 200 may be efficiently recaptured since the elongated valve support section are not engaging with the delivery catheter.

Figure 12:
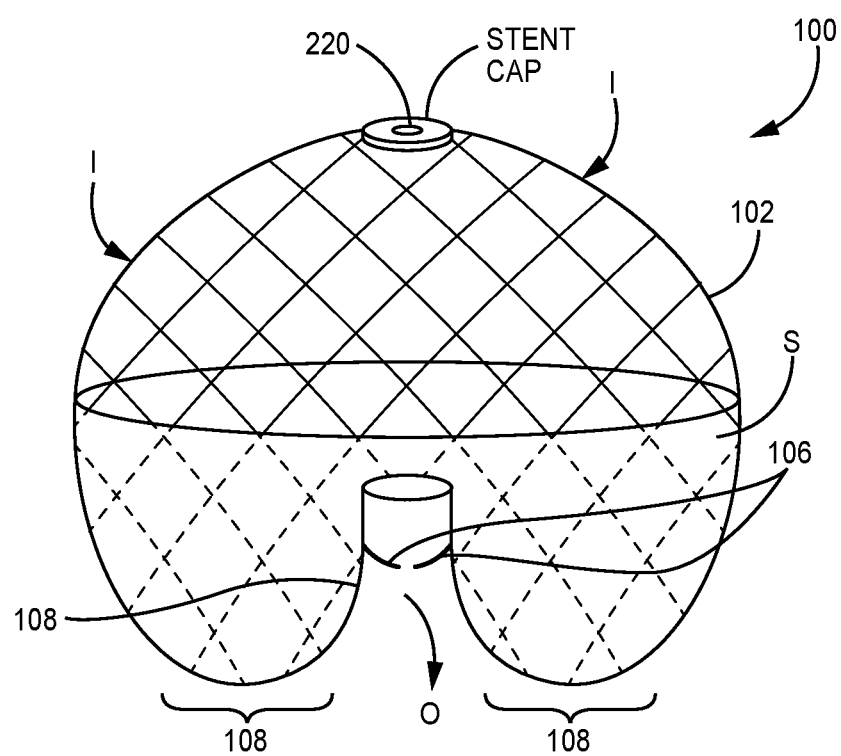
FIG. 12 illustrates a side and partial cutaway view of a prosthetic heart valve device of the present invention.

Turning now to FIG. 12, an exemplary embodiment is illustrated of an expandable and collapsible prosthetic heart valve stent 100 may comprise an outer section 102 that may generally look like a ball when undeformed and fully expanded and an inner valve support section 104, adapted to support and retain prosthetic valve leaflets 106 within the inner valve support section 104, most preferably at a point that located above the native annulus, and spaced away or above the native leaflets, as shown, though other attachment points for the prosthetic leaflets 106 are within the scope of the present invention. Inner valve support 104 may be cylindrical, but in a preferred embodiment may also be at least partially conical with a larger diameter at an outflow end O than the diameter across at least portions of an inflow end I, wherein the inflow end I is disposed radially inside the outer frame section and wherein the outflow end may define a lower end or edge of the valve support 104. Thus, in a purely conical arrangement, the valve support section 104 may comprise a smoothly decreasing diameter thereacross and this smooth diameter decrease may extend from the outflow end O to the inflow end I. In other embodiments, the inflow end I may comprise one or more lobes extending radially outwardly and that interrupt the smooth conical profile. A preferred embodiment in this regard provides one lobe for each prosthetic leaflet 106 attached within the inner valve support 104 to allow for fuller freedom of movement and improved coaptation.

A preferred construction comprises the prosthetic leaflets 106 disposed or spaced above the native leaflets when the prosthetic valve stent device 100 is implanted, wherein the prosthetic leaflets 106 are attached and spaced sufficiently away from (above) the native leaflets so as to not physically interfere or interact with the native leaflets and the resulting blood flow.

The layer of stent cells that transition from the outer section to the inner section of the stent are termed as transition cells forming a transition section 108 generally as illustrated in FIG. 12.

The outer and inner sections of the stent may be constructed from one continuous structure or may combine two or more structures to achieve intended design goals. As known in the art, stent structures may be formed using complementary shaped mandrels, including the outer section 102 of the stent, the transition section 108, and the inner valve support 104—including lobes L discussed above in certain embodiments—as a single unitary structure.

In certain embodiments, the outer support structure may be positioned generally so that it engages with tissue and works to prevent paravalvular leakage (PVL). For example, the outer support structure of the prolapse prevention structure may engage, or be integrated with, the transition section described above to provide a barrier against PVL.

Further in this regard, a preferred embodiment of the device shown in the Figures comprises a skirt S, comprising fabric or tissue, disposed along a portion of the outer surface of the outer frame element 102 and that extends along the outer surface of the transition section 108 and along the inner surface, or inwardly facing surface, of the inner valve support 104 so that the skirt S is facing the flow channel defined therein from the inflow end I to the outflow end O.

The embodiment of FIG. 4, and certain embodiments of FIG. 5, comprises a top-most (or upstream) set of stent cells 101 in the valve support 104 that are generally directed in the upstream direction. Stated differently, the top-most set of stent cells of valve support 104 define the top of the valve support 104.

Figure 13:
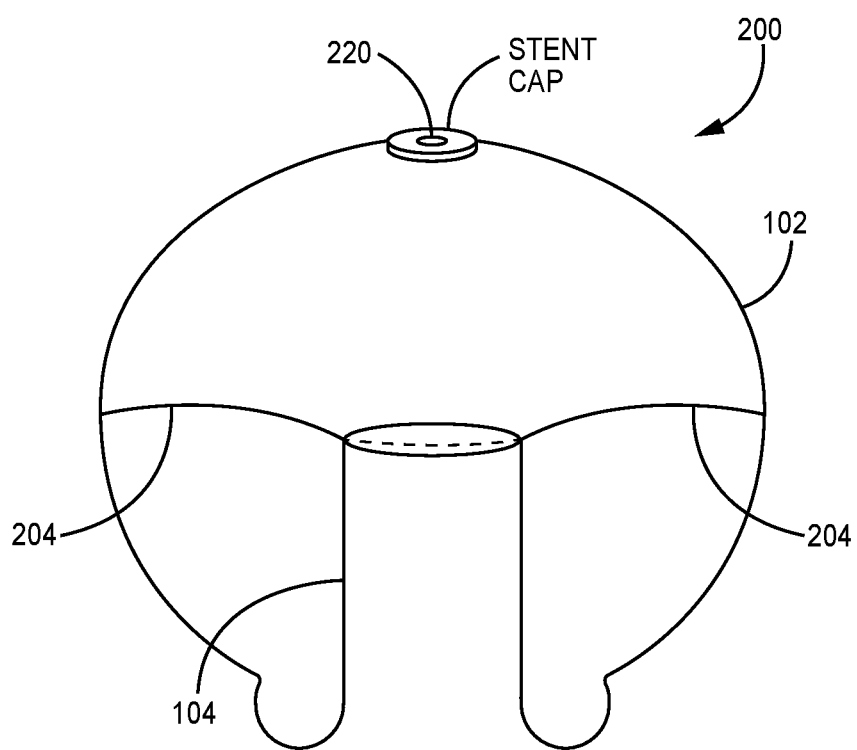
FIG. 13 illustrates a cutaway view of one embodiment of a prosthetic heart valve device of the present invention.

Turning now to FIG. 13, a modified and improved prosthetic heart valve device 200 is provided with the same elements as described above in connection with FIG. 12, except that the valve support 104 now comprises at least one, and preferably two (though more may be used) connectors 204 extending between the valve support 104 and the outer section 102 of stent device 200. As shown, the connectors 204 are connected at a first end to the valve support 104 at its top-most or upstream end, and at a second end connected to the outer section 102 of device 200. The connector(s) 204 may be heat set or may use a shape memory or other material as the skilled artisan will appreciate. The connector(s) 204 may be generally straight when connected and the device 200 is fully expanded, or they may be slightly bent to provide additional outward expanding force on the stent 200 which can assist in ensuring the implanted stent device 200 remains in place against the chamber walls. As shown, the connector(s) 204 are disposed within the interior defined by the outer section 102.

The first and second ends of the connector(s) 204 may be mechanically or otherwise attached to, or formed from, the valve support 104 and/or the outer section 102 of device 200. Exemplary connection methods, all well known to the artisan, include but are certainly not limited to, suturing, welding, riveting.

The stent cap shown in FIGS. 12 and 13 comprises a hole or slot 220 for engaging a delivery wire such as a push and/or pull wire to aid in delivery and recapture and/or repositioning of the collapsible and expandable stent device 200.

The various structural modifications described herein allow the valve support 104 to collapse inwardly more efficiently during both loading of the device 200 into the lumen of a delivery catheter as well as at least partial recapture when necessary of an at least partially expanded device 200 in order to reposition and/or reexpand and/or reimplant the device 200.

Though this structure may be most advantageous in a transseptal delivery technique and access to, e.g., the left atrium and mitral valve, other delivery access routes, techniques and heart valves may also be amenable to the improved structure and related advantages of device 200.

It is noteworthy that the various embodiments of the presently described prosthetic valve stent device 200 may be delivered percutaneously via one of at least the following known access and delivery routes: femoral access, venous access, trans-apical, trans-aortic, trans-septal, and trans-atrial, retrograde from the aorta delivery techniques. Alternatively, the prosthetic valve stent device 200 may be delivered and implanted using surgical and/or open heart techniques.

Various embodiments of the inventive concepts described herein comprise:

1. A prosthetic heart valve device, adapted for expansion and implantation into a heart chamber of a patient for supplementation and/or replacement of native valve leaflet functionality, the device comprising:
   a collapsible and expandable stent having an outer section comprising an outer surface, an inner surface, and defining an interior;
   a valve support operationally connected to the collapsible and expandable stent, wherein the valve support extends radially upward into the interior of the outer section and comprising an inflow end and an outflow end, the inflow end extending radially upward into the outer section, wherein a blood flow channel is defined between the inflow and outflow ends, and wherein the valve support is inverted entirely within the interior of the outer section,
   a plurality of prosthetic valve leaflets disposed within the blood flow channel defined by the valve support section, wherein prosthetic valve leaflets are configured to allow flow from the inflow end to the outflow end of the flow channel and prevent flow from the outflow end of the flow channel to the inflow end of the flow channel,
   wherein the valve support comprises a top section that is defined by a plurality of single struts that are bent radially inwardly over the blood flow channel.

2. The device of embodiment 1, wherein the valve support is defined and formed by the collapsible and expandable stent.

3. The device of embodiment(s) 1 and 2, further comprising transition cells that turn the outer section of the collapsible and expandable stent radially inwardly, the transition cells disposed between the outer section of the collapsible and expandable stent and the valve support.

4. The device of embodiment(s) 1-3, wherein the valve support and outer section of the valve support comprise a single unitary stent.

5. The device of embodiment(s) 1-4, wherein at least one of the plurality of single struts comprises a recapture assist mechanism.

6. The device of embodiment 5, wherein the recapture assist mechanism comprises an open paddle adapted for receiving a wire therethrough.

7. A method for delivery, recapturing and/or positioning the collapsible and expandable prosthetic heart valve device of embodiment(s) 1-6 into a heart chamber of a patient, comprising:
   providing a delivery catheter having a lumen therethrough;
   placing the delivery catheter within the patient such that a distal end of the delivery catheter and lumen are within the heart chamber and a proximal end of the delivery catheter and lumen are outside the patient's body;
   collapsing and loading the prosthetic heart valve device into a proximal end of the delivery catheter lumen and translating the prosthetic heart valve device distally;
   delivering the prosthetic heart valve device from the distal end of the delivery catheter lumen at least partially into the heart chamber;
   at least partially expanding the prosthetic heart valve device within the heart chamber; and
   when properly positioned, implanting the prosthetic heart valve device within the chamber.

8. The method of embodiment 7, further comprising providing at least one push and/or pull wire comprising a distal end that is operatively engaged with at least one of the recapture assist mechanism(s).

9. The method of embodiment 8, further comprising manipulating the push and/or pull wire(s) to modify the position of at least the valve support during expansion, positioning, recapturing and/or implanting of the prosthetic heart valve device.

10. The method of embodiment(s) 7-9, wherein the heart chamber comprises the left atrium.

11. The method of embodiment 10, wherein the prosthetic heart valve device is implanted and adapted to supplement the native mitral valve leaflet functionality.

12. The method of embodiment(s) 10 and 11, wherein the prosthetic heart valve device is implanted and adapted to supplement and eventually fully replace the native mitral valve leaflet functionality.

13. The method of embodiment(s) 7-10 wherein the delivery catheter is placed within the patient using the transseptal delivery access route.

14. The method of embodiment(s) 7-10, wherein the delivery catheter is placed within the patient using one of the access routes in the group consisting of: transapical; transfemoral; transatrial.

Additional embodiments of the various inventive concepts described herein further comprise:

1. A prosthetic heart valve device, adapted for expansion and implantation into a heart chamber of a patient for supplementation and/or replacement of native valve leaflet functionality, the device comprising:
   a collapsible and expandable stent having an outer section comprising an outer surface, an inner surface, and defining an interior and comprising a stent cap disposed at an upper portion of the outer section, the stent cap adapted to connect with a delivery wire;
   a valve support operationally connected to the collapsible and expandable stent, wherein the valve support extends radially upward into the interior of the outer section and comprising an inflow end and an outflow end, the inflow end extending radially upward into the outer section, wherein a blood flow channel is defined between the inflow and outflow ends, and wherein the valve support is inverted entirely within the interior of the outer section, a plurality of prosthetic valve leaflets disposed within the blood flow channel defined by the valve support section, wherein prosthetic valve leaflets are configured to allow flow from the inflow end to the outflow end of the flow channel and prevent flow from the outflow end of the flow channel to the inflow end of the flow channel, wherein the valve support comprises an elongated section extending in the upstream direction within the interior of the outer section.

2. The device of embodiment 1, wherein the valve support is defined and formed by the collapsible and expandable stent.

3. The embodiment(s) of claims 1 and 2, further comprising transition cells that turn the outer section of the collapsible and expandable stent radially inwardly, the transition cells disposed between the outer section of the collapsible and expandable stent and the valve support.

4. The device of embodiments 1-3, wherein the valve support and outer section of the valve support comprise a single unitary stent.

5. The device of embodiment(s) 1-4, wherein the elongated section of the valve support is operatively connected with the stent cap.

6. The device of embodiment(s) 1-5, wherein the elongated section of the valve support comprises a recapture and/or delivery assist mechanism disposed or defined thereon.

7. The device of embodiment 6, wherein the recapture assist mechanism comprises an open loop or open paddle adapted for receiving a wire therethrough.

8. A method for delivery, recapturing and/or positioning the collapsible and expandable prosthetic heart valve device of claims 1-7 into a heart chamber of a patient, comprising:
providing a delivery catheter having a lumen therethrough;
placing the delivery catheter within the patient such that a distal end of the delivery catheter and lumen are within the heart chamber and a proximal end of the delivery catheter and lumen are outside the patient's body;
collapsing and loading the prosthetic heart valve device into a proximal end of the delivery catheter lumen and translating the prosthetic heart valve device distally;
delivering the prosthetic heart valve device from the distal end of the delivery catheter lumen at least partially into the heart chamber;
at least partially expanding the prosthetic heart valve device within the heart chamber, wherein a portion of the elongated valve support section remains within the delivery catheter lumen; and
when properly positioned, implanting the prosthetic heart valve device within the chamber.

9. The method of embodiment 8, further comprising providing at least one push and/or pull wire comprising a distal end that is operatively engaged with at least one of the recapture assist mechanism(s); and adjusting or manipulating the position of the elongated valve support section with the at least one push and/or pull wire.

10. The exemplary method of embodiment 9, further comprising manipulating the push and/or pull wire(s) to modify the position of at least the valve support during expansion, positioning, recapturing and/or implanting of the prosthetic heart valve device.

11. The method of embodiment(s) 7-10, wherein the heart chamber comprises the left atrium.

12. The method of embodiment 11 wherein the prosthetic heart valve device is implanted and adapted to supplement the native mitral valve leaflet functionality.

13. The method of embodiment(s) 11 or 12, wherein the prosthetic heart valve device is implanted and adapted to supplement and eventually fully replace the native mitral valve leaflet functionality.

14. The method of embodiment(s) 7-13 wherein the delivery catheter is placed within the patient using the transseptal delivery access route.

15. The method of embodiment(s) 7-13, wherein the delivery catheter is placed within the patient using one of the access routes in the group consisting of: transapical; transfemoral; and transatrial.

Still further additional embodiments of the various inventive concepts described herein further comprise:

1. A prosthetic heart valve device, adapted for expansion and implantation into a heart chamber of a patient for supplementation and/or replacement of native valve leaflet functionality, the device comprising:
a collapsible and expandable stent having an outer section comprising an outer surface, an inner surface, and defining an interior and comprising a stent cap disposed at an upper portion of the outer section, the stent cap adapted to connect with a delivery wire;
a valve support operationally connected to the collapsible and expandable stent, wherein the valve support extends radially upward into the interior of the outer section and comprising an inflow end and an outflow end, the inflow end extending radially upward into the outer section, wherein a blood flow channel is defined between the inflow and outflow ends, and wherein the valve support is inverted entirely within the interior of the outer section,
a plurality of prosthetic valve leaflets disposed within the blood flow channel defined by the valve support section, wherein prosthetic valve leaflets are configured to allow flow from the inflow end to the outflow end of the flow channel and prevent flow from the outflow end of the flow channel to the inflow end of the flow channel; and
at least one collapsible and expandable connecting strut disposed between the valve support and the outer section, the at least one connecting strut located in the interior of the outer section and connected with the valve support at a first end and with the outer section at a second end.

2. The device of embodiment 1, wherein the valve support is defined and formed by the collapsible and expandable stent.

3. The device of embodiment(s) 1 and 2, further comprising transition cells that turn the outer section of the collapsible and expandable stent radially inwardly, the transition cells disposed between the outer section of the collapsible and expandable stent and the valve support.

4. The device of embodiment(s) 1-3, wherein the valve support and outer section of the collapsible and expandable stent comprise a single unitary stent.

5. The device of embodiment(s) 1-4, wherein the at least one collapsible and expandable connecting strut is heat set in position.

6. The device of embodiment(s) 1-5 wherein the at least one collapsible and expandable strut is formed from the valve support or the outer section of the collapsible and expandable stent.

7. The device of embodiment(s) 1-6, wherein at least one end of the at least one collapsible and expandable strut is connected to the valve support and/or the outer section of the collapsible and expandable stent.

8. The device of embodiment(s) 1-7, wherein the at least one connecting strut is operatively disposed at, or proximate, the inflow end of the valve support.

9. The device of embodiment(s) 1-7, wherein the at least one connecting strut is operatively disposed along the valve support at a location between the inflow end and the outflow end of the valve support.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A prosthetic heart valve device, adapted for expansion and implantation into a heart chamber of a patient for supplementation and/or replacement of native valve leaflet functionality, the device comprising:
   a collapsible and expandable stent having an outer section comprising an outer surface, an inner surface, and defining an interior;
   a valve support operationally connected to the collapsible and expandable stent, wherein the valve support extends radially upward into the interior of the outer section and comprises an inflow end and an outflow end, wherein a blood flow channel is defined between the inflow end and the outflow end, and wherein the valve support is inverted entirely within the interior of the outer section; and
   a plurality of prosthetic valve leaflets disposed within the blood flow channel defined by the valve support, wherein the prosthetic valve leaflets are configured to allow flow from the inflow end to the outflow end of the flow channel and prevent flow from the outflow end of the flow channel to the inflow end of the flow channel;
wherein:
   the inflow end of the valve support comprises a plurality of top-most stent cells that are bent radially inwardly over the blood flow channel;
   the valve support comprises a plurality of stent cells that are not the top-most stent cells; and
   at least one of the plurality of stent cells that are not the top-most stent cells further comprises at least one recapture assist mechanism disposed thereon.

2. The device of claim 1, wherein the valve support is defined and formed by the collapsible and expandable stent.

3. The device of claim 1, further comprising transition cells that turn the outer section of the collapsible and expandable stent radially inward, the transition cells being disposed between the outer section of the collapsible and expandable stent and the valve support.

4. The device of claim 2, further comprising transition cells that turn the outer section of the collapsible and expandable stent radially inward, the transition cells disposed between the outer section of the collapsible and expandable stent and the valve support.

5. The device of claim 1, wherein the valve support and the outer section of the valve support comprise a single unitary stent.

6. The device of claim 1, wherein the at least one recapture assist mechanism is configured to engage a wire to assist in one or more of the group consisting of: directional positioning during delivery of the device; recapture of the device during delivery; and resheathing of the device during delivery.

7. The device of claim 6, wherein the wire comprises a push and/or pull wire.

8. The device of claim 7, wherein the recapture assist mechanism comprises an open paddle adapted to engage the wire.

9. The device of claim 7, wherein the recapture assist mechanism comprises a slot adapted to engage the wire.

10. A method for delivery, recapturing and/or positioning the prosthetic heart valve device of claim 1 into a heart chamber of a patient, the method comprising:
    providing:
       a delivery catheter having a lumen therethrough;
       the at least one recapture assist mechanism; and
       at least one push and/or pull wire comprising a distal end that is operatively engaged with the at least one recapture assist mechanism;
    placing the delivery catheter within the patient such that a distal end of the delivery catheter and lumen are within the heart chamber and a proximal end of the delivery catheter and lumen are outside the patient's body;
    collapsing and loading the prosthetic heart valve device into a proximal end of the delivery catheter lumen and translating the prosthetic heart valve device distally;
    delivering the prosthetic heart valve device from the distal end of the delivery catheter lumen at least partially into the heart chamber;
    at least partially expanding the prosthetic heart valve device within the heart chamber; and
    implanting the prosthetic heart valve device within the heart chamber.

11. The method of claim 10, further comprising manipulating at least one of the at least one push and/or pull wires to modify a position of at least the valve support during expansion, positioning, recapturing and/or implanting of the prosthetic heart valve device.

12. The method of claim 10, wherein the heart chamber is the left atrium.

13. The method of claim 10, wherein the prosthetic heart valve device, when implanted, is adapted to supplement the native mitral valve leaflet functionality.

14. The method of claim 10, wherein the prosthetic heart valve device, when implanted, is adapted to supplement and eventually replace the native mitral valve leaflet functionality.

15. The method of claim 10, wherein the delivery catheter is placed within the patient using a transseptal delivery access route.

16. The method of claim 10, wherein the delivery catheter is placed within the patient using one of the access routes in the group consisting of: transapical; transfemoral; and transatrial.

17. The method of claim 10, wherein the prosthetic heart valve device, when implanted, is adapted to replace the native mitral valve leaflet functionality.

* * * * *